US010905869B2

(12) United States Patent
Tennican (10) Patent No.: US 10,905,869 B2
(45) Date of Patent: Feb. 2, 2021

(54) ANTIMICROBIAL COMPOSITION INCLUDING A RESIDUAL BARRIER FILM

(71) Applicant: Hyprotek, Inc., Spokane, WA (US)

(72) Inventor: Patrick O. Tennican, Spokane, WA (US)

(73) Assignee: Hyprotek, Inc., Spokane, WA (US)

( * ) Notice: Subject to any disclaimer, the term of this patent is extended or adjusted under 35 U.S.C. 154(b) by 1257 days.

(21) Appl. No.: 13/688,078

(22) Filed: Nov. 28, 2012

(65) Prior Publication Data

US 2013/0136801 A1 May 30, 2013

Related U.S. Application Data

(60) Provisional application No. 61/564,206, filed on Nov. 28, 2011.

(51) Int. Cl.
| | | |
|---|---|---|
| A01N 59/00 | (2006.01) | |
| A61M 39/16 | (2006.01) | |
| A61K 33/40 | (2006.01) | |
| A61M 11/08 | (2006.01) | |
| A61M 15/08 | (2006.01) | |
| A61M 39/20 | (2006.01) | |
| A61M 25/00 | (2006.01) | |
| A61K 9/00 | (2006.01) | |
| A61K 47/18 | (2017.01) | |
| A61M 35/00 | (2006.01) | |

(52) U.S. Cl.
CPC ........... *A61M 39/162* (2013.01); *A01N 59/00* (2013.01); *A61K 33/40* (2013.01); *A61M 11/08* (2013.01); *A61M 15/08* (2013.01); *A61M 25/002* (2013.01); *A61M 25/0017* (2013.01); *A61M 39/20* (2013.01); *A61K 9/0014* (2013.01); *A61K 47/183* (2013.01); *A61M 35/00* (2013.01); *A61M 39/165* (2013.01); *A61M 2025/0019* (2013.01); *A61M 2205/583* (2013.01); *A61M 2209/06* (2013.01); *F04C 2270/0421* (2013.01); *Y10S 604/905* (2013.01)

(58) Field of Classification Search
None
See application file for complete search history.

(56) References Cited

U.S. PATENT DOCUMENTS

| | | | |
|---|---|---|---|
| 3,648,704 A | 3/1972 | Jackson | |
| 4,334,551 A | 6/1982 | Pfister | |
| 4,360,020 A | 11/1982 | Hitchcock, Jr. et al. | |
| 4,811,847 A | 3/1989 | Reif et al. | |
| 5,048,684 A | 9/1991 | Scott | |
| 5,226,530 A | 7/1993 | Golden | |
| 6,090,075 A | 7/2000 | House | |
| 7,780,794 B2 | 8/2010 | Rogers et al. | |
| 7,981,090 B2 | 7/2011 | Plishka et al. | |
| 8,336,152 B2 | 12/2012 | Vaillancourt et al. | |
| 2001/0001443 A1 | 5/2001 | Kayerod et al. | |
| 2005/0265773 A1 | 12/2005 | De Laforcade | |
| 2007/0161949 A1 | 7/2007 | Knox et al. | |
| 2007/0213645 A1 | 9/2007 | Zumeris et al. | |
| 2007/0282280 A1* | 12/2007 | Tennican | 604/246 |
| 2008/0019889 A1 | 1/2008 | Rogers et al. | |
| 2008/0033371 A1 | 2/2008 | Updegraff et al. | |
| 2008/0132880 A1 | 6/2008 | Buchman | |
| 2009/0024111 A1 | 1/2009 | Borodulin et al. | |
| 2009/0028750 A1 | 1/2009 | Ryan | |
| 2009/0299334 A1 | 12/2009 | Nishtala et al. | |
| 2009/0324508 A1 | 12/2009 | Bobbert | |
| 2010/0242993 A1 | 9/2010 | Hoang et al. | |
| 2011/0030726 A1 | 2/2011 | Vaillancourt et al. | |
| 2011/0052664 A1 | 3/2011 | Tennican et al. | |
| 2011/0064512 A1 | 3/2011 | Shaw et al. | |
| 2011/0171280 A1* | 7/2011 | Toreki | D06M 11/155 424/411 |
| 2011/0201692 A1 | 8/2011 | Raad | |
| 2011/0301553 A1 | 12/2011 | Goral et al. | |
| 2013/0030414 A1 | 1/2013 | Gardner et al. | |

FOREIGN PATENT DOCUMENTS

| | | |
|---|---|---|
| CN | 1717261 | 1/2006 |
| CN | 1806746 | 7/2006 |
| CN | 101306221 | 11/2008 |
| CN | 101405042 | 4/2009 |
| CN | 101505815 | 8/2009 |
| CN | 101618384 | 1/2010 |

(Continued)

OTHER PUBLICATIONS

PCT Search Report dated Apr. 1, 2013 for PCT application No. PCT/US12/66886, 13 pages.
PCT Search Report dated Feb. 26, 2013 for PCT application No. PCT/US12/66894, 11 pages.
PCT Search Report dated Mar. 4, 2013 for PCT application No. PCT/US12/66880, 12 pages.
Chinese Office Action dated Aug. 28, 2015 for Chinese patent application No. 201280058307.6, A counterpart foreign application of U.S. Appl. No. 13/688,044, 16 pages.
Australian Office Action dated Oct. 7, 2015 for Australian patent application No. 2012346043, a counterpart foreign application of U.S. Appl. No. 13/688,044, 3 pages.

(Continued)

*Primary Examiner* — Jake M Vu
(74) *Attorney, Agent, or Firm* — Lee & Hayes, P.C.

(57) ABSTRACT

This disclosure describes example antimicrobial compositions that may be used in combination with IV port cleansing caps, protective caps, or nasal decolonizer devices. According to another implementations, the disclosure describes that the antimicrobial composition may provide an indication that it has come into contact with a contaminant by bubbling or foam on a surface that is being cleaned. According to another implementation, the disclosure describes that the antimicrobial composition may leave a residual film or barrier to inhibit the recontamination of a surface that has been cleaned.

18 Claims, 4 Drawing Sheets

(56) References Cited

FOREIGN PATENT DOCUMENTS

| CN | 101878050 | 11/2010 |
|---|---|---|
| DE | 29608617 | 8/1996 |
| JP | 2000153876 | 6/2000 |
| JP | 2003261177 | 9/2003 |
| JP | 2007089599 | 4/2007 |
| JP | 2000056273 | 3/2009 |
| JP | 2009537250 | 10/2009 |
| JP | 2013503713 | 2/2013 |
| JP | 2013518056 | 5/2013 |
| KR | 20090003267 | 1/2009 |
| WO | WO2000025846 | 5/2000 |
| WO | WO0165939 | 9/2001 |
| WO | WO2003064279 | 8/2003 |
| WO | WO2006071781 | 7/2006 |
| WO | WO2007137056 | 11/2007 |
| WO | WO2009076718 | 6/2009 |
| WO | WO2010002757 | 1/2010 |
| WO | WO2011022601 | 2/2011 |
| WO | WO2011028965 | 3/2011 |
| WO | WO2011053924 | 5/2011 |
| WO | WO2011091322 | 7/2011 |
| WO | WO2011109393 | 9/2011 |

OTHER PUBLICATIONS

Chinese Office Action dated Sep. 14, 2015 for Chinese patent application No. 201280058316.5, a counterpart foreign application of U.S. Appl. No. 13/688,044, 22 pages.
European Office Action dated Sep. 25, 2015 for European patent application No. 12853916.0, a counterpart foreign application of U.S. Appl. No. 13/688,044, 3 pages.
European Office Action dated Sep. 25, 2015 for European patent application No. 12852866.8, a counterpart foreign application of U.S. Appl. No. 13/688,078, 3 pages.
European Office Action dated Sep. 25, 2015 for European patent application No. 12852889.0, a counterpart foreign application of U.S. Appl. No. 13/688,073, 3 pages.
Chinese Office Action dated Feb. 14, 2016 for Chinese patent application No. 201280058307.6, a counterpart foreign application of U.S. Appl. No. 13/688,044, 16 pages.
Chinese Office Action dated Feb. 6, 2016 for Chinese patent application No. 201280058316.5, a counterpart foreign application of U.S. Appl. No. 13/688,044, 29 pages.
Final Office Action for U.S. Appl. No. 13/688,044, dated Oct. 30, 2015, Patrick O. Tennican, "Port and Surface Cleaning Devices and Techniques", 10 pages.
Australian Office Action dated Nov. 26, 2015 for Australian patent application No. 2012346043, a counterpart foreign application of U.S. Appl. No. 13/688,044, 3 pages.
Chinese Office Action dated Nov. 13, 2015 for Chinese patent application No. 201280058237.4, a counterpart foreign application of U.S. Appl. No. 13/688,044, 18 pages.
Extended European Search Report dated Jan. 14, 2016 for European Patent Application No. 12852889.0, 9 pages.
Extended European Search Report dated Jan. 7, 2016 for European Patent Application No. 12852866.8, 8 pages.
Extended European Search Report dated Jan. 7, 2016 for European patent application No. 12853916.0, 9 pages.
Chinese Office Action dated Oct. 25, 2016 for Chinese Patent Application No. 201280058237.4, a counterpart foreign application of U.S. Appl. No. 13/688,044, 17 pages.
European Office Action dated Oct. 25, 2016 for European Patent Application No. 12852889.0, a counterpart foreign application of U.S. Appl. No. 13/688,073, 4 pages.
Chinese Office Action dated May 11, 2016 for Chinese patent application No. 201280058316.5, a counterpart foreign applicaton of U.S. Appl. No. 13/688,044, 28 pages.
Chinese Office Action dated May 5, 2016 for Chinese Patent Application No. 201280058237.4, a counterpart foreign application of U.S. Appl. No. 13/688,044, 18 pages.
Office action for U.S. Appl. No. 13/688,044, dated Apr. 1, 2016, Tennican, "Port and Surface Cleaning Devices and Techniques", 10 pages.
European Office Action dated Sep. 8, 2016 for European Patent Application No. 12852866.8, a counterpart foreign application of U.S. Appl. No. 13/688,078, 4 pages.
Australian Office Action dated Jul. 11, 2016 for Australian patent application No. 2012346036, a counterpart foreign application of U.S. Appl. No. 13/688,044, 4 pages.
Australian Office Action dated Jul. 19, 2016 for Australian Patent Application No. 2012346043, a counterpart foreign application of U.S. Appl. No. 13/688,044, 3 pages.
Chinese Office Action dated Jul. 4, 2016 for Chinese patent application No. 201280058307,6, a counterpart foreign application of U.S. Appl. No. 13/688,044, 15 pages.
Office action for U.S. Appl. No. 13/688,044, dated Aug. 19, 2016, Tennican, "Port and Surface Cleaning Devices and Techniques", 9 pages.
Austrlian Office Action dated Oct. 25, 2016 for Australian Patent Application No. 2012346036, a counterpart foreign application of U.S. Appl. No. 13/688,044, 3 pages.
Chinese Office Action dated Sep. 28, 2016 for Chinese patent application No. 201280058316.5, a counterpart foreign application of U.S. Appl. No. 13/668,044, 24 pages.
Japanese Office Action dated Sep. 20, 2016 for Japanese Patent Application No. 2014-543628, a counterpart foreign application of U.S. Appl. No. 13/688,044, 13 pages.
Japanese Office Action dated Sep. 20, 2016 for Japanese Patent Application No. 2014-543627, a counterpart foreign application of U.S. Appl. No. 13/688,073, 13 pages.
Japanese Office Action dated Oct. 4, 2016 for Japanese Patent Application No. 2014-543631, a counterpart foreign application of U.S. Appl. No. 13/688,078, 13 pages.
Chinese Office Action dated Apr. 28, 2017 for Chinese patent application No. 201280058316.5, a counterpart foreign application of U.S. Appl. No. 13/668,044, 20 pages.
Chinese Office Action dated Jan. 23, 2017 for Chinese Patent Application No. 201280058307.6, a counterpart foreign application of U.S. Appl. No. 13/688,044, 15 pages.
Japanese Office Action dated Jan. 24, 2017 for Japanese Patent Application No. 2014-543631, a counterpart foreign application of U.S. Appl. No. 13/688,078, 4 pages.
Australian Office Action dated Oct. 14, 2016 for Australian Patent Application No. 2012346030, a counterpart foreign application of U.S. Appl. No. 13/688,073, 4 pages.
Office action for U.S. Appl. No. 13/688,044, dated Jan. 12, 2017, Tennican, "Port and Surface Cleaning Devices and Techniques", 8 pages.
Australian Office Action dated Sep. 28, 2017 for Australian Patent Application No. 2012346030, a counterpart foreign application of U.S. Appl. No. 13/688,073, 6 pages.
Office action for U.S. Appl. No. 13/888,044, dated Jun. 21, 2017, Tennican, "Port and Surface Cleaning Devices and Techniques", 9 pages.
Australian Office Action dated Jul. 31, 2017 for Australian Patent Application No. 2012346030, a counterpart foreign application of U.S. Appl. No. 13/688,073, 8 pages.
Japanese Office Action dated Jun. 13, 2017 for Japanese Patent Application No. 2014-543627, a counterpart foreign application of U.S. Appl. No. 13/688,073, 10 pages.
Japanese Office Action dated Jun. 27, 2017 for Japanese Patent Application No. 2014-543628, a counterpart foreign application of U.S. Appl. No. 13/688,044, 9 pages.
Office action for U.S. Appl. No. 13/688,044, dated Dec. 20, 2017, Tennican, "Port and Surface Cleaning Devices and Techniques", 12 pages.
Chinese Office Action dated Nov. 7, 2017 for Chinese patent application No. 201280058307.6, a counterpart foreign application of U.S. Appl. No. 13/688,073, 11 pages.
Mexican Office Action dated Oct. 9, 2017 for Mexican patent application No. MX/a/2014/006413, a counterpart foreign application of U.S. Appl. No. 13/688,044.

(56) References Cited

OTHER PUBLICATIONS

Japanese Office Action dated Dec. 25, 2017 for Japanese Patent Application No. 2014-543627, a counterpart foreign application of U.S. Appl. No. 13/688,073.
Japanese Office Action dated Dec. 19, 2017 for Japanse patent application No. 2014-543628, a counterpart foreign application of U.S. Appl. No. 13/688,044.
Non-Final Office Action for U.S. Appl. No. 13/688,073, dated May 23, 2013, Patrick O. Tennican, "Catheter Devices and Techniques", 13 pages.
Hooton et al, "Diagnosis, Prevention, and Treatment of Catheter-Associated Urinary Tract Infection in Adults: 2009 Intl Clinical Practice Guidelines from the Infectious Disease Society of America", Mar. 2010, Urinary Catheter Guidelines, Clinical Infectious Diseases, vol. 50, 39 pgs.
Final Office Action for U.S. Appl. No. 13/688,073, dated Jan. 15, 2015, Patrick O. Tennican, "Catheter Devices and Techniques", 18 pages.
Office Action for U.S. Appl. No. 13/688,073, dated Sep. 12, 2014, Patrick O. Tennican, "Catheter Devices and Techniques", 12 pages.
Office Action for U.S. Appl. No. 13/688,073, dated Oct. 25, 2013, Patrick O. Tennican, "Catheter Devices and Techniques", 11 pages.
Chinese Office Action dated Mar. 31, 2015 for Chinese patent application No. 201280058237.4, a counterpart foreign application of U.S. Appl. No. 13/688,044, 20 pages.
Office Action for U.S. Appl. No. 13/688,044, dated May 28, 2015, Patrick O. Tennican, "Port and Surface Cleaning Devices and Techniques", 9 pages.
Final Office Action for U.S. Appl. No. 13/688,073, dated Apr. 18, 2014, Patrick O. Tennican, "Catheter Devices and Techniques", 13 pages.

\* cited by examiner

ANTIMICROBIAL COMPOSITION INCLUDING A RESIDUAL BARRIER FILM

CROSS REFERENCE TO RELATED APPLICATION

This claims priority to U.S. Provisional Patent Application No. 61/564,206 filed on Nov. 28, 2011, entitled "Medical Devices and Techniques for Antiseptic, Immunomodulatory and Antineoplastic Therapies," which is hereby incorporated by reference in its entirety.

BACKGROUND

Infection remains a real problem in the medical industry today. Infections are often caused by contamination of intravascular (IV) lines (e.g., intravenous, intra-arterial, etc.), contamination of an injection site or blood draw site (e.g., from a vein, artery, or capillary), urinary catheters, wound sites, incision sites, and numerous other sources of infection in healthcare facilities. For example, in United States hospitals alone, central venous catheters cause an estimated 250,000 blood stream infections per year, which result substantial costs, both in terms of financial resources consumed and in patient morbidity. O'Grady, MD, et al., *Guidelines for the Prevention of Intravascular Catheter-Related Infections,* 2011, Center for Disease Control, Department of Health and Human Services. These numbers do not include infections caused contamination of injection sites, blood draw sites, non-venous catheters, or any of the other numerous sources of contamination in healthcare facilities. Infection is even more of a problem in developing nations, where syringes, IV lines, and other equipment routinely are used and re-used for multiple different patients.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

Overview

This application describes approaches to reducing and/or preventing infections. In one aspect, the application describes example antimicrobial compositions that may be used alone or in combination with one or more medical devices to clean and/or disinfect intravascular (IV) line ports, other IV components (e.g., syringes, lumens, valves, etc.), injection sites, blood draw sites (e.g., from a vein, artery, or capillary), catheters and/or catheter insertion sites, wound sites, incision sites, peritoneal dialysis sites, bladder or nephrostomy sites, other drainage sites, or any other site that is susceptible to infection.

Example Antimicrobial Composition

In one example implementation, antimicrobial compositions that may be used in connection with the approaches described herein may include those described in, for example, U.S. patent application Ser. No. 12/874,188, filed Sep. 1, 2010, to Tennican et al., which is incorporated herein by reference. In that case, the antimicrobial compositions may include water ($H_2O$), a strong and non-toxic chelating agent such as ethylenediaminetetraacetic acid (EDTA) (e.g., disodium EDTA, calcium disodium EDTA, magnesium EDTA, gallium EDTA) or sodium citrate (or acids, salts, derivatives, or other forms of EDTA or sodium citrate), a short-chain monohydric alcohol (e.g., ethanol with a molecular formula of $C_2H_5OH$ and an empirical formula of $C_2H_6O$), and a strong, small molecule oxidizing agent such as hydrogen peroxide ($H_2O_2$). In one specific example, the compositions may consist essentially of water, EDTA, ethanol, and hydrogen peroxide. However, in other examples, other antimicrobial compositions may be used in combination with the devices described in this application.

The antimicrobial compositions may be in a liquid form, a gel form, or a foam form, for example, and may be combined with one or more carriers or diluents, depending on the needs of a specific application. For example, in applications in which the antimicrobial composition is used as a hand sanitizer, the antimicrobial composition may be in a gel form. As another example, if the antimicrobial composition is used as a cleaning agent, a flush solution, or an irrigant, the antimicrobial composition may be in a liquid form. In that case, the concentration of the various constituents may depend on, for example, a desired level of disinfection, whether the composition is being applied directly to living tissue or to a medical device, and/or to avoid irritation of tissue to which the composition will be applied directly or indirectly (e.g., via a medical device to which the composition is or was applied). In another example, a liquid form of the antimicrobial compositions may be vaporized or sprayed for application to nasal passages or other airways of a patient. In yet another example, the antimicrobial compositions may include or be combined with a lubricant (e.g., glycerin), surfactant or emulsifier (e.g., glycerol monolaurate (GML)), or the like and may be applied to a catheter, tracheal tube, scope, instrument, or other device that is to be inserted into a patient's body.

Example Film or Barrier Layer

In addition to providing disinfection at the time of the application, the antimicrobial compositions may also provide a lasting barrier against contamination. For example, even after volatile constituents of the composition (e.g., water, alcohol, hydrogen peroxide, etc.) have evaporated, the chelating agent may remain on the treated surfaces (e.g., port, port cleaning/protecting device, fingers, surrounding tissue, etc.) as a barrier that will provide antibacterial, antifungal or sporicidal (e.g., preventing germination of the spores), anti-parasitic, and antiviral qualities. By robbing the environment of components (e.g., iron, magnesium, and manganese) that are needed for the bacterial, spores, parasites, and viruses to reproduce, the chelating agent provides a lasting defense to contamination even after other constituents of the antimicrobial composition have evaporated. Furthermore, the hydrogen peroxide in the antimicrobial compositions may induce a charge on a surface of materials (e.g., silicone materials) to which the antimicrobial compositions are applied, which make the materials more resistant to bacteria or other microorganisms.

Figure 1:
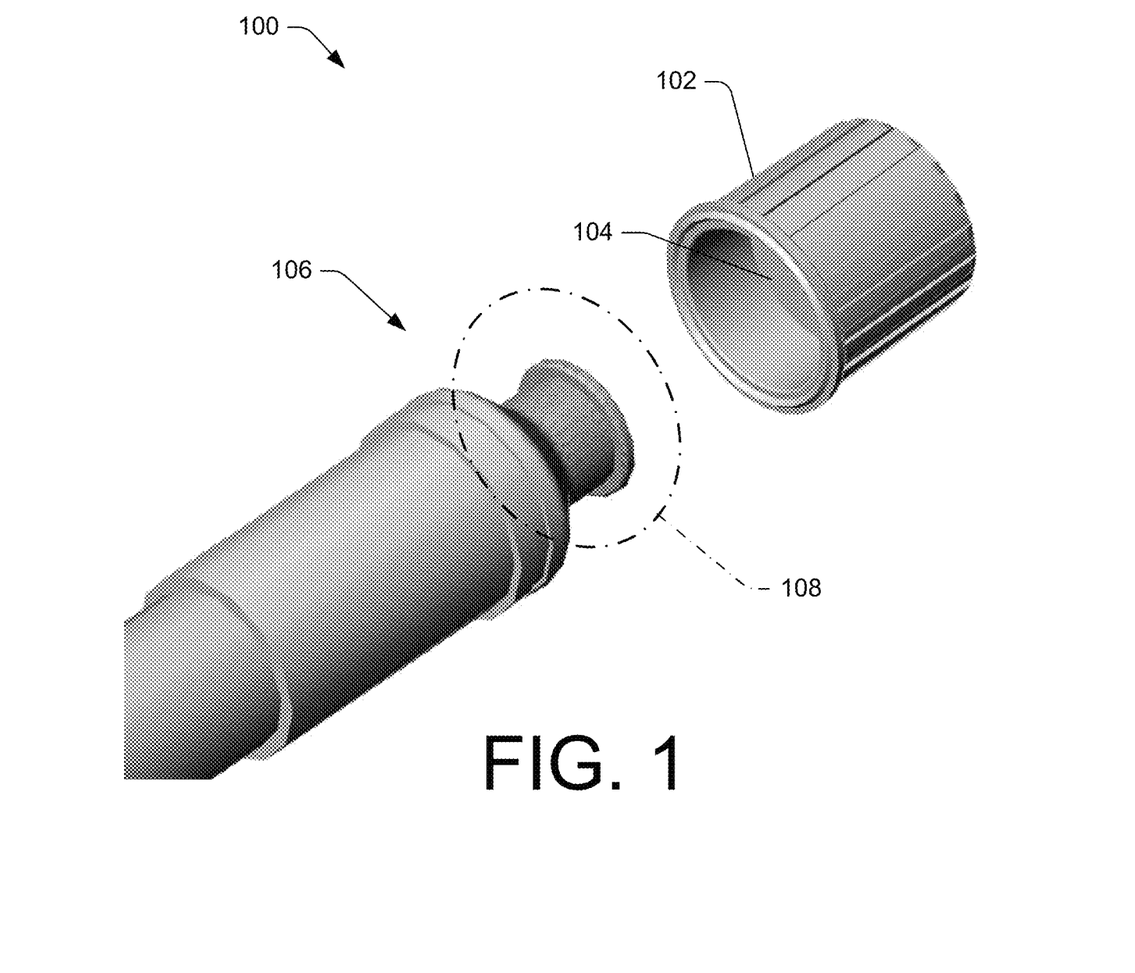
FIG. 1 illustrates an example port cleaning system that may include a cleaning cap having an applicator material carrying an antimicrobial composition.

FIG. 1 illustrates an example IV port cleaning system 100 including a cleaning cap 102 having an applicator material 104 carrying an antimicrobial composition, such as those described above. The cleaning cap 102 may be used to clean an IV port 106. In the illustrated example, the IV port comprises a female Luer® connector. However, in other embodiments, such IV port cleaning systems may be used or adapted for use in cleaning male Luer-Lok® or Luer® connectors, as well as other types of IV and non-IV ports and/or lumens. The cleaning cap 102 may be used to disinfect the IV port 106, for example, prior to connecting the port to a complimentary port, injecting a medication, drawing blood, or otherwise using the IV port 106. After being disinfected, volatile constituents of the antimicrobial composition may evaporate over time, leaving a film or barrier layer 108 of EDTA or other chelating agent that, as described above, provides a lasting defense to contamination.

Once disinfected, a protective cap (not shown in this figure) may be applied to the IV port 106 to provide a physical barrier against recontamination. The protective cap may contain a same or different antimicrobial composition or other composition. In some implementations, the protective cap may securely couple to the IV port 106 and may seal the IV port. In the event that the antimicrobial composition in the protective cap dries out over time, the protective cap may still include a residual barrier layer of EDTA or other chelating agent that will provide further defense to contamination. In other embodiments, instead of one of the antimicrobial compositions described above, the protective cap may simply be coated with a film or barrier layer of EDTA or other chelating agent over all or part of the interior and/or exterior surfaces of the protective cap.

While FIG. 1 illustrates an embodiment of an IV port cleaning system that includes a cleaning cap 102, in other embodiments, other cleaning devices may be used to carry and apply antimicrobial compositions according to this disclosure. By way of example and not limitation, other cleaning devices that may be used include pads, swabs, wipes, sponges, or any other material capable of carrying an antimicrobial composition. Further, while FIG. 1 illustrates the antimicrobial composition and cap system being used to clean an IV port, antimicrobial compositions and cleaning devices according to this disclosure may be used to clean and/or disinfect other IV components, injection sites, blood draw sites, catheter and/or catheter insertion sites, wound sites, incision sites, peritoneal dialysis sites, drainage sites, or any other sites that are susceptible to infection.

Furthermore, in addition to their cleaning, disinfecting, and barrier properties, the antimicrobial compositions described above may include one or more therapeutic uses, such as those described herein below, as well as those described in International Patent Application No. PCT/US2011/022150, filed Jan. 21, 2011, to Tennican et al., which is incorporated herein by reference.

Example Indicator of Contamination

In addition to their cleaning, disinfecting, barrier properties, and therapeutic uses, the antimicrobial compositions described above provide a visual indicator of contamination, which may allow medical providers to identify and clean or replace contaminated equipment to prevent infection. Details of this indicator functionality are described below with respect to an example IV port cap system of FIGS. 2A-2C and 3A-3C. However, the indicator functionality of the antimicrobial compositions is not limited to such a system and is applicable regardless of the system or procedure in which the antimicrobial compositions are used.

Figures 2A, 2B, 2C:
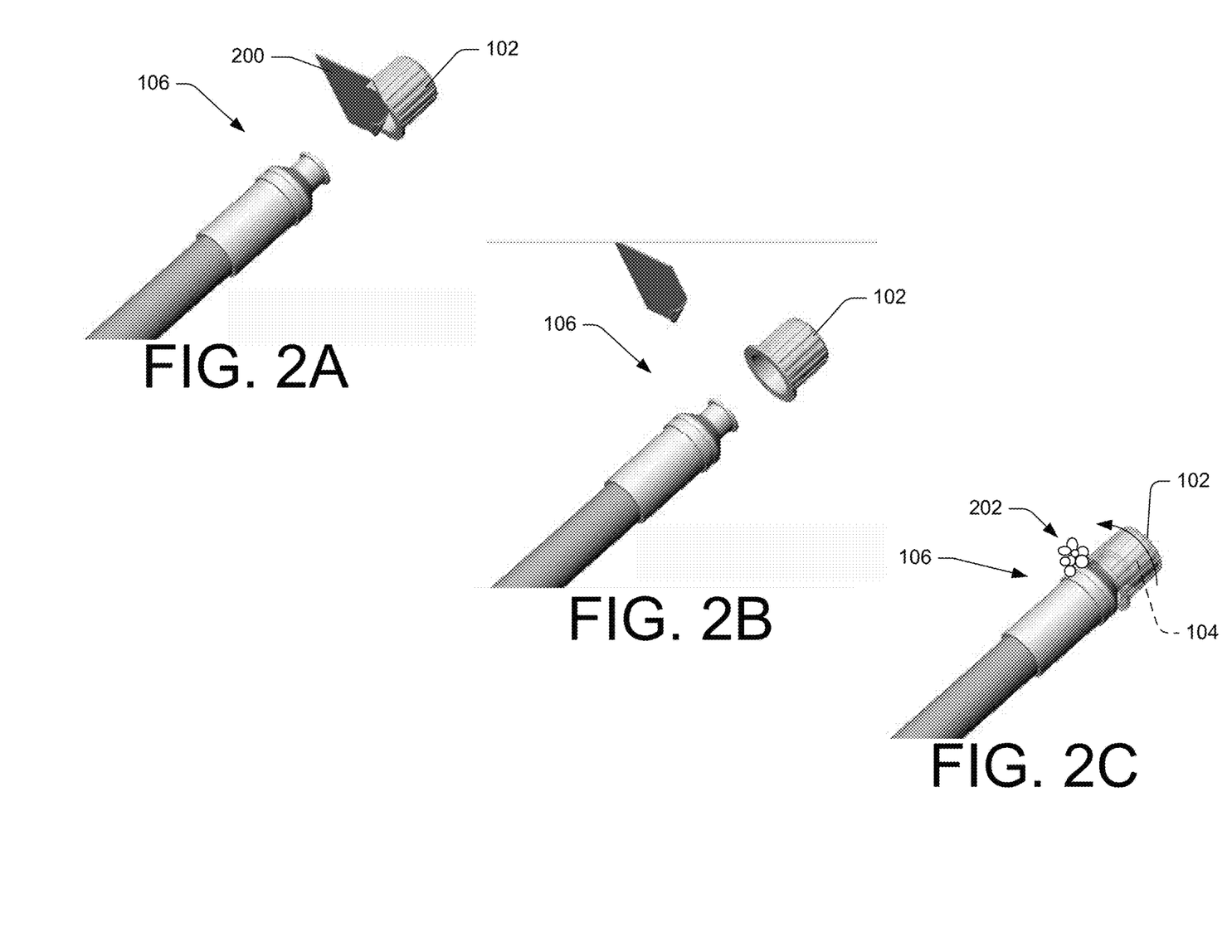
FIGS. 2A-2C illustrate example port cleaning and disinfection system where the antimicrobial composition may give a visual indication of contaminants.

FIGS. 2A-2C illustrate the IV port cleaning and disinfection system 100 of FIG. 1 in more detail. Specifically, FIG. 2A illustrates the cleaning cap 102 prior to use. As shown in FIG. 2A, the cleaning cap 102 may come with a protective cover 200 that maintains the interior of the cleaning cap 102 in a sterile condition. Additionally or alternatively, the cleaning cap 102 may come packaged within another sterile package (not shown in this figure) to maintain the entire cleaning cap 102 in a sterile condition prior to use. In order to use the cleaning cap 102 to clean the IV port 106, the protective seal may be removed, exposing the interior of the cap 102, as shown in FIG. 2B. The cleaning cap 102 may then be placed onto the IV port 106 and twisted or otherwise used to scrub and clean the IV port 106. Specifically, the applicator material 104 carrying the antimicrobial composition may be used to scrub the exterior surfaces of the IV port 106 by twisting and pressing the cleaning cap 102 against the IV port 106.

If the IV port 106 is contaminated with bacteria, spores, parasites, viruses, bodily fluids, or other contaminants, the antimicrobial composition will begin to bubble or foam 202, providing a visual indicator of the contamination. The bubbling or foaming action is caused by reaction of the hydrogen peroxide with the bacteria, spores, parasites, and viruses. Specifically, contaminant enzymes that cause the hydrogen peroxide in the antimicrobial compositions to foam include but are not limited to, for example, catalases, superoxide dismutases (SOD), glutathione peroxidases, peroxiredoxin, and other peroxidases. Ooropharyngeal, respiratory, cervicovaginal secretions and serum would also contain hydrogen peroxide reactants or enzymes that would cause the antimicrobial compositions to foam. EDTA may attenuate these reactions somewhat. However, testing shows that the attenuation is mild and does not impair the ability of the antimicrobial compositions to visually indicate the presence of contamination. For example, *Staphylococcus aureus* (MRSA) with catalase and *Pseudomonas aeruginosa* with SOD both produce vigorous bubbling on contact with antimicrobial compositions according to this application. The hydrogen peroxide will also produce bubbles or foam in response to a Fenton reaction with iron in the hemoglobin in red blood cells, or peroxidases in white blood cells and in the bodily fluids. The size and rate of bubble formation may be indicative of the level of contamination, giving the medical personnel a visual indication that the equipment is contaminated and a relative degree to which the equipment is contaminated (e.g., more or larger bubbles/foam indicates more contamination). Based on this indication medical personnel may determine that the equipment needs further cleaning and/or replacement to avoid infection.

Figures 3A, 3B, 3C:
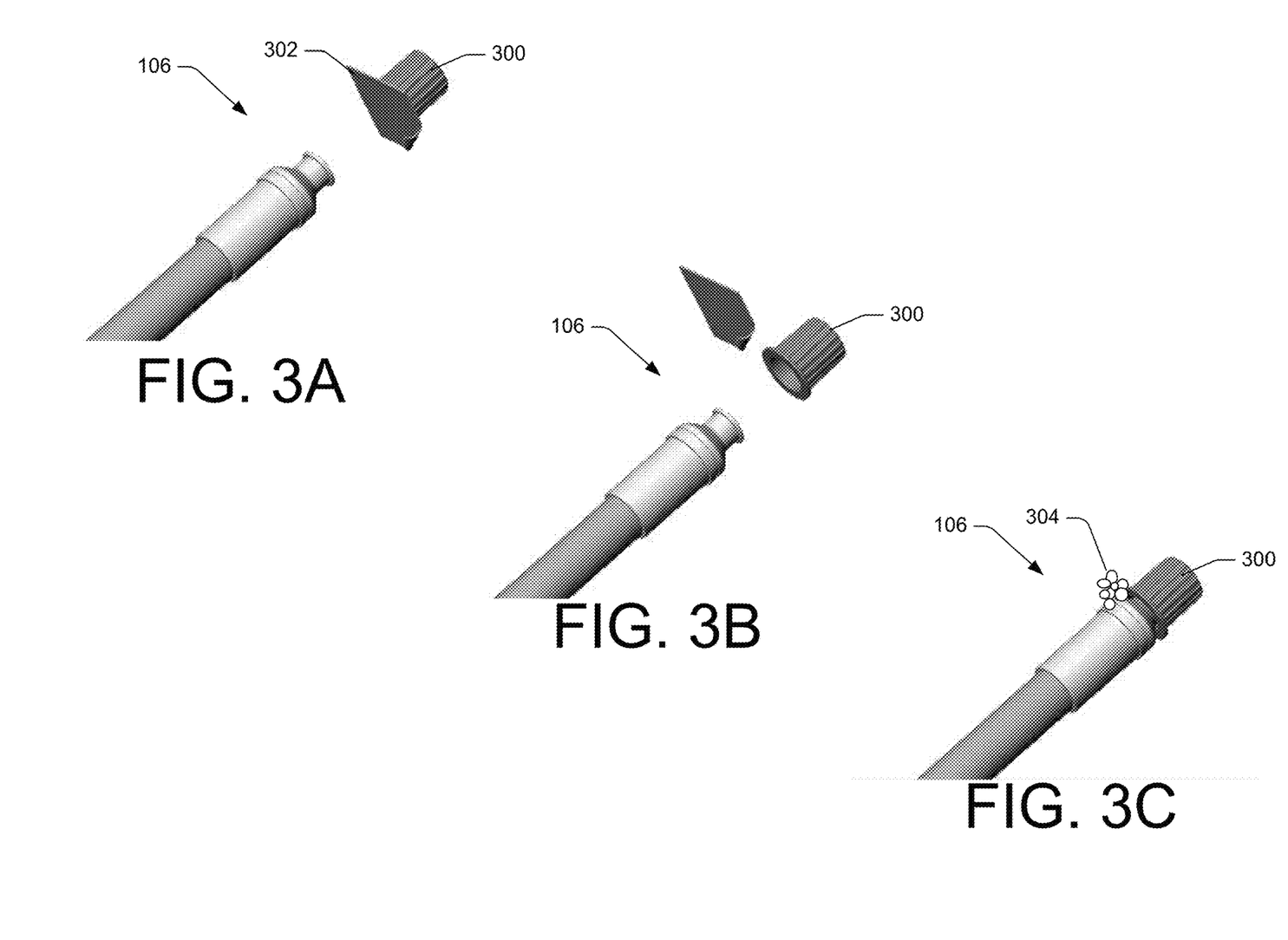
FIGS. 3A-3C illustrate example protective cap where the antimicrobial composition may give a visual indication of contaminants.

FIGS. 3A-3C illustrate an example protective cap 300 that may in some embodiments be used in combination with the cleaning cap 102 of FIG. 1 and FIGS. 2A-2C. After the IV port 106 has been cleaned, a protective cover 302 may be removed from the protective cap 300 to expose the interior of the protective cap, as shown collectively in FIGS. 3A and 3B. As with the cleaning cap 102, the protective cap 300 may come packaged within another sterile package (not shown in this figure) to maintain the entire protective cap 300 in a sterile condition prior to use.

The protective cap 300 may then be applied to the IV port 106 to provide a physical barrier against recontamination, as shown in FIG. 3C. The protective cap 300 may contain a same or different antimicrobial composition or other composition than the cleaning cap 102. If, when the protective cap 300 is coupled to the IV port 106, bubbling or foaming 304 occurs, this bubbling or foaming will provide a visual indicator to medical personnel that the IV port 106 is still contaminated and needs further cleaning and/or replacement.

In some embodiments, the antimicrobial composition in the cleaning cap 102 the protective cap 300, or both may include a dye or colorant that serves to further enhance the visual indication of contamination. When provided, the dye or colorant in the cleaning cap 102 may be the same or different color than that in the protective cap 300. For example, the dye or colorant may be of a color to match the color of the respective cap. In another example, the dye or colorant may be of a color to contrast with the color of the respective cap.

Example Nasal/Oropharyngal Devices

Figure 4:
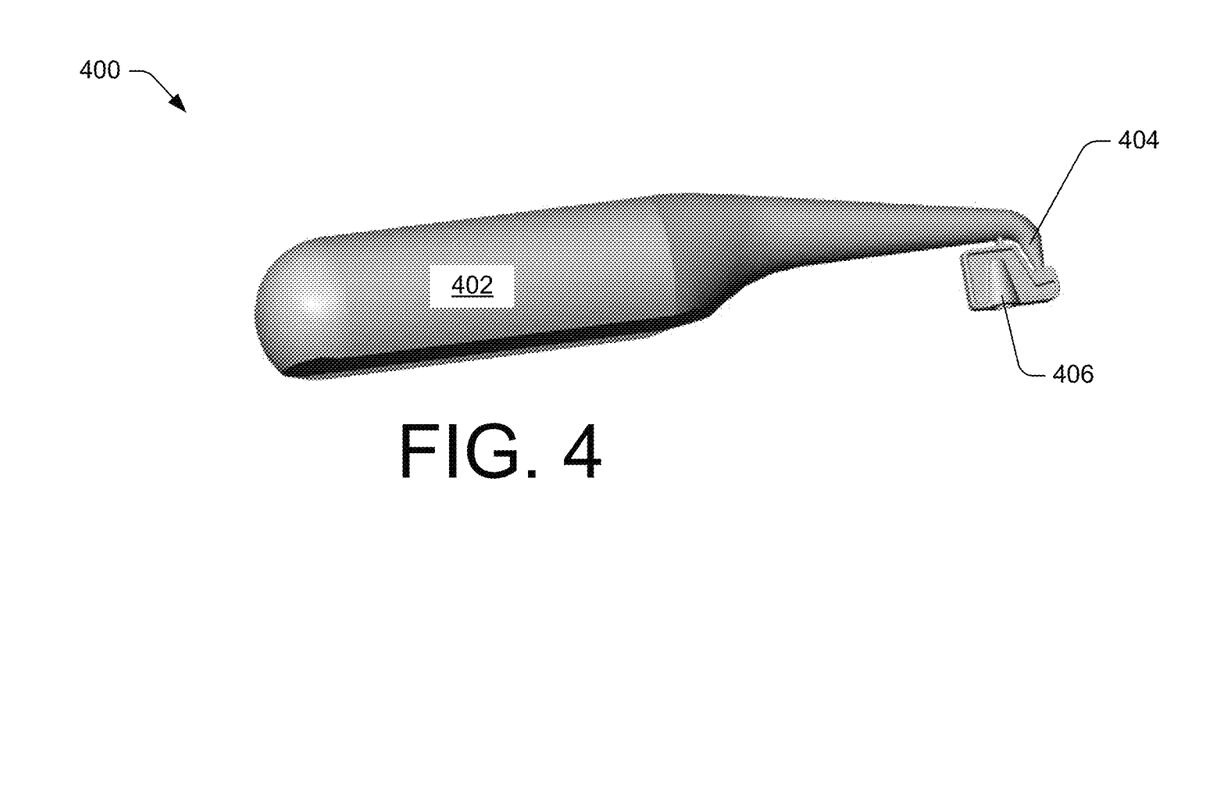
FIG. 4 illustrates an example nasal decolonizer device that may be used to deliver a antimicrobial composition.

FIG. 4 illustrates a nasal decolonizer device 400 that may be used to deliver antimicrobial compositions such as those described herein to nasal passages of a patient. The antimicrobial compositions of this embodiment may include concentrations of alcohol and hydrogen peroxide that are lower than those used in the port and site cleaning and disinfecting applications due to the more sensitive nature of the nasal passages. The nasal decolonizer device 400 may be used to apply the antimicrobial compositions to areas of nasal and oropharyngeal passageways of MRSA, or other resistant bacteria, carriers and/or prior to elective surgical implants. The antimicrobial compositions may be dispensed as a spray or gel.

As illustrated in FIG. 4, the nasal decolonizer device 400 includes a reservoir 402 to hold an antimicrobial composition and a dispensing spout 404 sized and shaped to fit at least partially into a nasal passage of a patient. The dispensing spout 404 may be made of a relatively soft, pliable material, which may serve in some implementations as an applicator or spreader of the gel or liquid to accessible inner surfaces of the nose and/or nasal passages. Prior to use, the dispensing spout 404 is capped by a frangible tab 406 that hermetically seals the nasal decolonizer device 400.

The nasal decolonizer 400 or other medical device of varying size, shape, material, and configuration, with a dispensing spout for spray or gel contained in a reservoir, may be used to deliver antimicrobial, immunomodulatory, and/or antineoplastic therapy to internal body sites or hard to reach sites.

CONCLUSION

Although the application describes embodiments having specific structural features and/or methodological acts, it is to be understood that the claims are not necessarily limited to the specific features or acts described. Rather, the specific features and acts are merely illustrative some embodiments that fall within the scope of the claims of the application.

What is claimed is:

1. A method of giving a visual indication of one or more contaminants on a surface comprising:
    determining the surface to be decontaminated; and
    testing the surface for contamination, the testing including:
        applying an antimicrobial agent to the surface, wherein the antimicrobial agent comprises water, an alcohol, a peroxide or peroxide-generating agent, a chelating agent, and a colorant; and
        receiving the visual indication that that the antimicrobial agent has come in contact with the one or more contaminants on the surface, the visual indication resulting from the contact and including at least an appearance of a color.

2. The method as recited in claim 1, wherein the surface to be decontaminated comprises human tissue or an area on a medical device.

3. The method as recited in claim 1, wherein:
    the chelating agent includes about 5 to about 50 mg/ml of ethlyenediaminetetraacetic acid (EDTA);
    the alcohol includes at most about 70% ethanol, by volume; and
    the peroxide or peroxide-generating agent includes at most about 7.5% hydrogen peroxide, by volume.

4. The method as recited in claim 1, wherein the one or more contaminants comprises at least one of one or more bacteria, one or more spores, one or more parasites, one or more viruses, one or more bodily fluids.

5. The method as recited in claim 4, wherein the one or more contaminants includes *Staphylococcus aureus* (MRSA), *Pseudomonas aeruginosa* and other resistant bacteria.

6. The method as recited in claim 1, wherein an amount of the chelating agent present in the antimicrobial agent does not inhibit the indication that the antimicrobial agent has come in contact with one or more contaminants on the surface.

7. The method as recited in claim 1, wherein the indication additionally includes at least one of:
    foaming; or
    bubbling.

8. A contaminant detection method, comprising:
    applying to a surface an antimicrobial agent including: water, an alcohol, a peroxide or peroxide-generating agent, a chelating agent, and a colorant; and
    observing the surface visually to see whether an appearance of a color occurs in the antimicrobial agent at a time of the applying,
    wherein the appearance of the color indicates indicating that the antimicrobial agent has contacted a contaminant on the surface.

9. The method as recited in claim 8, wherein the observing further includes observing the surface visually to see at least one of foaming or bubbling.

10. The method as recited in claim 8, wherein the chelating agent in the antimicrobial agent includes about 5 to about 50 mg/ml of ethlyenediaminetetraacetic acid (EDTA).

11. The method as recited in claim 8, wherein the alcohol in the antimicrobial agent includes at most about 70% ethanol, by volume.

12. The method as recited in claim 8, wherein the peroxide or peroxide-generating agent in the antimicrobial agent includes at most about 7.5% hydrogen peroxide, by volume.

13. The method as recited in claim 8, wherein the surface includes an end of an IV port, and
    wherein the applying includes coupling a protective cap containing the antimicrobial agent therein on the end of the IV port.

14. A method of determining whether an apparatus needs cleansing or replacement due to contamination, the method comprising:
    testing a surface of the apparatus for contamination, the testing including:
        applying to a surface an antimicrobial agent including: water, an alcohol, a peroxide or peroxide-generating agent, a chelating agent, and a colorant, and
        observing the surface visually to see whether an appearance of a color occurs at the surface at a time of the applying the antimicrobial agent, where the appearance of the color indicates that the antimicrobial agent has come in contact with one or more contaminants on the apparatus; and determining whether additional cleansing or replacement of the apparatus is needed based, at least in part, on the observing of the surface.

15. The method as recited in claim 14, wherein the determining whether additional cleansing or replacement of the apparatus is needed is further based, at least in part, on the observing a size and rate of bubble formation at the surface, where an increase in the size or rate indicates greater contamination.

16. The method as recited in claim 14, wherein:

the chelating agent includes about 5 to about 50 mg/ml of ethlyenediaminetetraacetic acid (EDTA), and the alcohol includes at most about 70% ethanol, by volume.

17. The method as recited in claim 14, wherein the apparatus is an IV port.

18. The method as recited in claim 14, wherein the apparatus is a medical device.

\* \* \* \* \*